United States Patent
Guan et al.

(10) Patent No.: US 9,804,609 B2
(45) Date of Patent: Oct. 31, 2017

(54) MASS FLOW CONTROLLERS AND METHODS FOR AUTO-ZEROING FLOW SENSOR WITHOUT SHUTTING OFF A MASS FLOW CONTROLLER

(75) Inventors: Xiao-Sheng Guan, Shanghai (CN); Robert C. Henderson, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 344 days.

(21) Appl. No.: 14/380,641

(22) PCT Filed: Feb. 22, 2012

(86) PCT No.: PCT/CN2012/000229
§ 371 (c)(1),
(2), (4) Date: Nov. 10, 2014

(87) PCT Pub. No.: WO2013/123617
PCT Pub. Date: Aug. 29, 2013

(65) Prior Publication Data
US 2015/0168956 A1  Jun. 18, 2015

(51) Int. Cl.
G05D 7/06 (2006.01)
G01N 30/32 (2006.01)
G01F 25/00 (2006.01)

(52) U.S. Cl.
CPC ....... G05D 7/0635 (2013.01); G01F 25/0007 (2013.01); G01N 30/32 (2013.01)

(58) Field of Classification Search
CPC ............ G05D 7/0635; Y10T 137/7761; Y10T 137/87322; Y10T 137/8733;
(Continued)

(56) References Cited

U.S. PATENT DOCUMENTS 4,687,020 A    8/1987  Doyle
5,062,446 A *  11/1991 Anderson ............ G05D 7/0635
                                                    137/487.5
(Continued)

FOREIGN PATENT DOCUMENTS

CN    2689231 Y    3/2005
CN    202072764 U  12/2011
WO    2007086960 A1  8/2007

OTHER PUBLICATIONS

Search Report, Chinese Patent Application No. 201280070436.7, dated Aug. 23, 2015.
(Continued)

*Primary Examiner* — Eric Keasel

(57) ABSTRACT

An MFC includes: a proportional valve; a mass flow sensor; a first flow line connecting from an outlet of the proportional valve through the mass flow sensor to an exit line; a second flow line joining the first flow line at a first junction located upstream of the mass flow sensor and at a second junction located downstream of the mass flow sensor; a switching valve placed such that the switching valve can regulate a flow of a gas through the first flow line or the second flow line; and a control device connected to provide a feedback control loop for regulating the proportional valve based on signals measured by the mass flow sensor, wherein the control device includes a program for keeping a rate of a flow exiting the exit line substantially constant when the flow is through the second flow line.

10 Claims, 9 Drawing Sheets

(58) Field of Classification Search
CPC ..... Y10T 137/87338; Y10T 137/87354; Y10T 137/87507; G01F 25/0007; G01N 30/32
See application file for complete search history.

(56) References Cited

U.S. PATENT DOCUMENTS

| | | | |
|---|---|---|---|
| 5,065,794 A * | 11/1991 | Cheung | F17D 1/04 137/883 |
| 5,542,286 A | 8/1996 | Wang | |
| 5,661,225 A * | 8/1997 | Ridgeway | G01M 3/207 137/7 |
| 5,744,695 A * | 4/1998 | Forbes | G01F 25/0053 73/1.35 |
| 6,152,177 A | 11/2000 | Gerner | |
| 7,258,132 B2 | 8/2007 | Henderson | |
| 7,674,375 B2 | 3/2010 | Gerhardt | |
| 7,918,238 B2 | 4/2011 | Tanaka | |
| 2007/0233412 A1 | 10/2007 | Gotoh et al. | |

OTHER PUBLICATIONS

Search Report from the European Patent Office dated Oct. 20, 2015 for European Application No. 12869058.
International Search Report for PCT/CN2012/000229 dated Dec. 6, 2012.

* cited by examiner

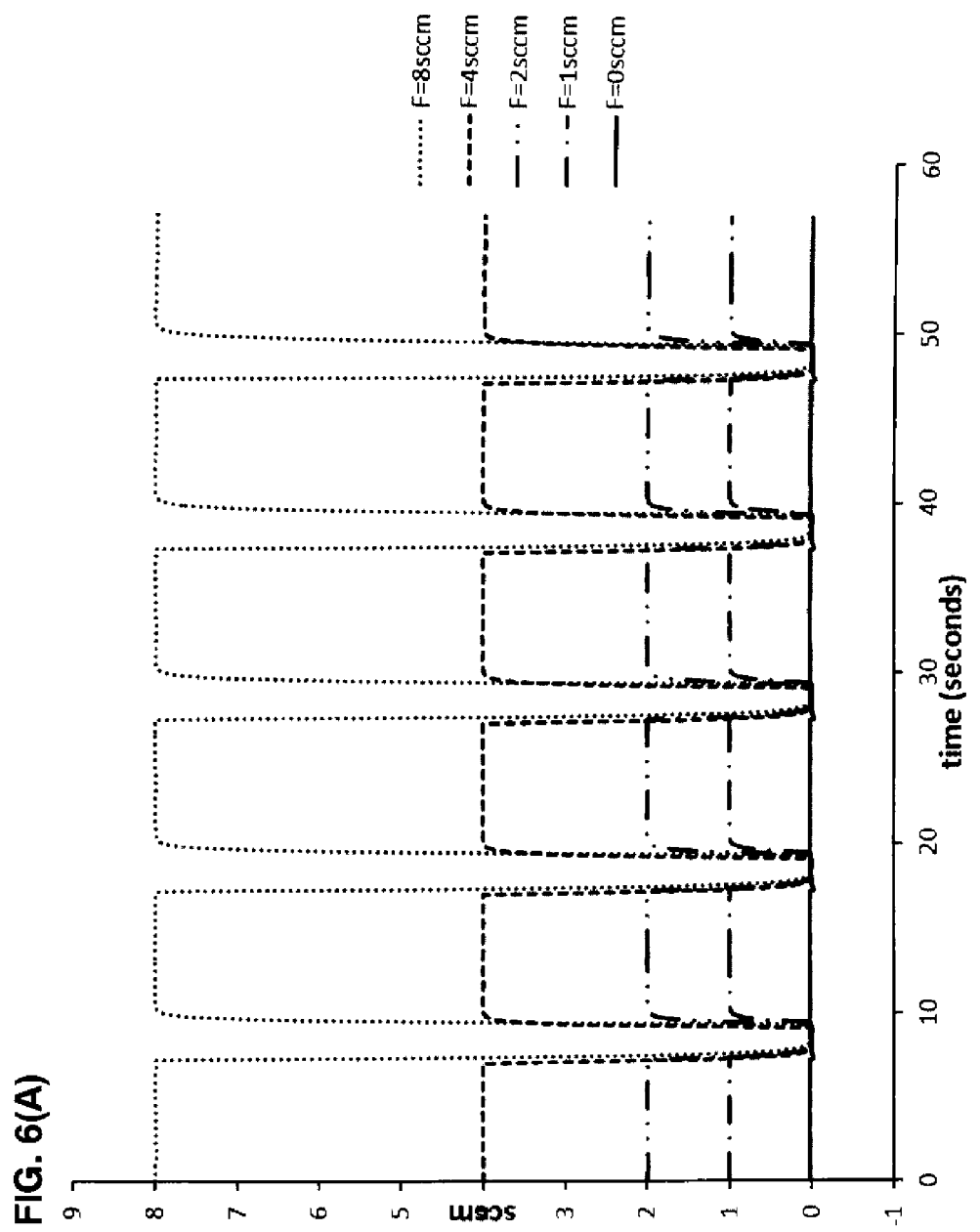

MASS FLOW CONTROLLERS AND METHODS FOR AUTO-ZEROING FLOW SENSOR WITHOUT SHUTTING OFF A MASS FLOW CONTROLLER

RELATED APPLICATIONS

This application is the national stage of International Application No. PCT/CN2012/000229, filed Feb. 22, 2012, titled "MASS FLOW CONTROLLERS AND METHODS FOR AUTO-ZEROING FLOW SENSOR WITHOUT SHUTTING OFF A MASS FLOW CONTROLLER," the content of which is incorporated herein by reference in its entirety.

FIELD OF THE INVENTION

This invention relates generally to the field of fluid flow control, particularly gas flow control, and more specifically, the invention relates to mass flow controllers and methods for auto-zeroing a mass flow sensor included therein.

BACKGROUND OF THE INVENTION

Control of a small mass flow rate of gas in a typical range from 1 standard cubic centimeter per minute (sccm) down to 0.1 sccm is challenging. However this is often required in a variety of industrial and analytical applications, such as semiconductor manufacturing and gas chromatography. A controller typically comprises a sensing device and a control device. The challenge comes from both sensing side and control side. The present invention addresses problems on sensing side.

FIG. 1 shows a schematic of a conventional mass flow controller (MFC) 100. In its simplest form, an MFC 100 consists of a proportional valve (PV) 101, a mass flow sensor (FS) 102, and control electronics (i.e., a control device) 103 to create a feedback loop. The mass flow sensor 102 measures the flow rates and sends the electric signals to the control device 103, which determines the flow rates based on the signals received. The determination often is based on comparison with a standard curve stored in the control device. Based on such determinations, the control device 103 then regulates the proportional valve 101 to produce the desired flow rates.

In FIG. 1, the mass flow sensor 102 is shown to be downstream of the proportional valve 101. In some designs, the mass flow sensor 102 may be upstream of the proportional valve 101. Furthermore, there are other MFCs that have the mass flow sensors in the form of a bypassing tube that passes a fixed fraction of what flows via a main passageway. The bypass tube design is typically used when it is desirable to expand the measurement ranges.

As noted above, a mass flow sensor (such as 102 shown in FIG. 1) produces flow dependent electric signals, which are used by the control electronics to determine appropriate regulation of the proportional valve (such as 101 shown in FIG. 1) in order to control the gas flow. The accuracy of the electric signals produced by the mass flow sensor is critical for the accurate control of the flows. Therefore, calibration is needed to establish a relation between such signals and actual mass flow rates, which are typically expressed in standard cubic centimeter per minute (sccm) or other equivalent units.

Calibration of a mass flow sensor starts with determining a sensor signal at zero-flow conditions (namely, the "zero-offset" value). Then, signals for several pre-defined non-zero flow rates are measured, and the zero-offset value is subtracted from the values of these signals to construct a calibration curve. Once such a calibration curve is created, it is usually stored in a non-volatile memory in the MFC and constantly referenced by the feedback loop control.

The above described setup and calibration generally work well when the flow rates are not too small. For small mass flow rates, it is difficult to measure the signals accurately by the mass flow sensors because these signals are close to the zero-offset, and it is difficult to keep a stable zero-offset regardless of the mass flow sensor types.

Zero-offset could be sensitive to many variables, such as temperatures, pressures, sensor mount orientations, etc, depending on the MFC designs. Most common and significant is the temperature sensitivity, followed by the pressure sensitivity, of the sensors. The sensors may also exhibit long-term drifting due to a variety of reasons, e.g., sensor internal stress relief. Consequently, zero-offset is commonly characterized by its temperature coefficient, pressure coefficient, and time coefficient, respectively, for commercial products.

Currently, temperature sensitivity may be reduced by a careful design of the temperature compensation circuitry, or by keeping a mass flow sensor in a controlled thermal zone. Pressure sensitivity may be addressed by additional calibration for the pressures.

Another strategy is to auto-zero mass flow sensors whenever possible and necessary. This strategy is implemented in some of the commercial instruments, such as Agilent 7890A Gas Chromatograph. Auto-zero is performed by shutting off the MFC proportional valve for a short period of time (e.g., 1.5-6 seconds at the end of each run) to create a zero (or near zero) flow condition. During the shut off, the mass flow sensor takes a measurement, and the newly acquired sensor signals are used to update the zero-offset values. Auto-zero is an effective way to correct for the long-term drifting or other changes (e.g., sudden changes). In addition, auto-zero is also a feasible approach to addressing the temperature and pressure variations.

However, the need to shut off the MFC proportional valve for auto-zero calibration means that auto-zero can only be safely carried out between active measuring or analytical processes, because flow control interruptions may produce detrimental effects. Furthermore, proportional valves in MFCs are usually not positive shut off valves. As a result, a certain amount of leak is always present, and any leak would introduce errors in the zero-offset. To ensure absolutely zero flow during an auto-zero process, additional positive shut off valves are required, either upstream or downstream or on both sides of the MFC. Such additional positive shut-off valves increase the overall system costs and complexity.

U.S. Pat. No. 5,542,286, issued to Wang et al., discloses a method of correcting flow and pressure sensor drifts in a gas chromatograph. In one of the embodiments described, when the GC is not being used, the input valve is shut, reducing the internal flow to zero. The indicated rate of flow is then measured using the flow sensor. In situations where the flow should not be interrupted, a three-way valve that can be used to direct flow away from the flow sensor during the calibration is described.

In the apparatus of the '286 patent, the flow controller is used to control total flow into the inlet. The low flow rates required for the chromatographic column and the septum purge flows are controlled by controlling the pressure to the column and the septum purge regulator. Because of this specific design and the apparatus uses the flow sensor to control total flow, changes in total flow from the flow controller may occur when the flow sensor is being bypassed. The '286 patent does not address ways to maintain the total flow at a constant value during calibration.

There are applications where it is important to control low flows of gases that cannot use pressure values to control the proportional valve during calibration. For applications that require accurate and precise control of low flow rates, there is a need to calibrate the sensor while continuing to adequately control the flow.

SUMMARY OF THE INVENTION

One aspect of the invention relates to mass flow controllers (MFCs). An MFC in accordance with one embodiment of the invention includes: a proportional valve having a first port connected to a first external line; a mass flow sensor; a first flow line connecting from second port of the proportional valve through the mass flow sensor to a second external line, wherein one of the first external line and the second external line is an entry line for connection to a fluid source and the other of the first external line and the second external line is an exit line of the MFC; a second flow line joining the first flow line at a first junction located upstream of the mass flow sensor and at a second junction located downstream of the mass flow sensor; a switching valve placed at the first junction or the second junction to join the first flow line and the second flow line such that the switching valve can regulate a flow of a gas through the first flow line or the second flow line; and a control device, wherein the control device is connected with the proportional valve and the mass flow sensor to provide a feedback control loop for regulating the proportional valve based on signals measured by the mass flow sensor, wherein the control device comprises a program for keeping a rate of a flow exiting the exit line substantially constant when the flow is through the second flow line.

In some embodiments, the control device is connected with the switching valve for controlling switching action of the switching valve. In some embodiments, the switching valve is connected to a separate control device for controlling the switching functions. In some embodiments, the proportional valve is upstream of the flow sensor, and in others, the proportional valve is downstream of the flow sensor.

In some embodiments, any MFC as described may further include a temperature sensor and/or a pressure sensor. In some embodiments, the temperature sensor may be integrated in the pressure sensor or the flow sensor.

Another aspect of the invention relates to methods for manufacturing a mass flow controller, which includes a proportional valve connected to a mass flow sensor via a first flow line and a control device for controlling the proportional valve based on signals measured by the mass flow sensor. A method in accordance with one embodiment of the invention includes: connecting a first end of a second flow line to the first flow line at a first junction; connecting a second end of the second flow line to a switching valve; and connecting the switching valve to the first flow line at a second junction, wherein one of the first junction and the second junction is located upstream of the mass flow sensor and the other is located downstream of the mass flow sensor, wherein the switching valve is configured to regulate a gas flow through the first flow line or the second flow line. The method may further include modifying a program in the control device such that the control device is configured to use a pseudo signal to control the proportional valve when the fluid flows through the second flow line. The method may further includes connecting the switching valve to a control device, which may be the same device for controlling the proportional valve or which may be a separate electronic control for the switching valve.

Another aspect of the invention relates to methods for performing auto-zeroing of a mass flow controller in accordance with embodiments of the invention. A method in accordance with one embodiment of the invention may include the following steps: controlling the switching valve such that a gas flows through the second flow line and bypasses the mass flow sensor; measuring a zero-flow signal using the mass flow sensor while the gas flows through the second flow line; and updating a zero-offset of the mass flow controller based on the zero-flow signal. In some embodiments, the method may hold the outlet flow rates substantially constant during the auto-zero processes, which may be accomplished by a signal sent from the control electronics (i.e., the control device) to the proportional valve.

Other aspects and advantages of the invention will be apparent from the following description and the appended claims.

BRIEF DESCRIPTION OF THE DRAWINGS

The accompanying drawings illustrate several embodiments of the invention and, together with the description, serve to explain the principles of the invention.

FIG. 6A shows results of auto-zeroing of MFCs of the invention at various flow rates.

DETAILED DESCRIPTION OF THE INVENTION

Embodiments of the present invention relate to MFCs and methods for auto-zeroing mass flow sensors without need to shut off MFC proportional valves interrupting output flow.

Embodiments of the invention provide true zero flows so an accurate zero-offset can be obtained, while controlling the flow at the outlet at substantially constant rates. Embodiments of the invention also allow auto-zero to be conducted at any time, even during active control periods (i.e., normal operation mode), because there is no need to shut off the gas flow during the auto-zeroing. Therefore, embodiments of the invention may be used as a single means for compensating zero-offset shifts caused by many different reasons (e.g., long-term drifts, temperature changes, pressure changes, etc.).

While embodiments of the invention can be used for fluid (i.e., liquid and gas) control, the following description may use "gas" flow control to illustrate embodiments of the invention. However, such references to "gas" are for clarity of illustration only, and one skilled in the art would appreciate that such description may also apply to "liquid" flow controls.

As used herein, the term "substantially constant" refers to a value that changes or varies by not more than 5% in the aggregate or average flow over a time period that is 10 times longer than the time that the flow control is in the switched away position, preferably no more than 3%, more preferably no more than 1%.

In accordance with embodiments of the invention, an MFC is provided with a bypass gas flow line and a switching valve. The bypass flow line allows the gas flow to bypass the mass flow sensor (or "flow sensor"), and the switching valve is used to control the flow of the gas (i.e., to bypass the mass flow sensor or not to bypass the mass flow sensor).

Figure 1:
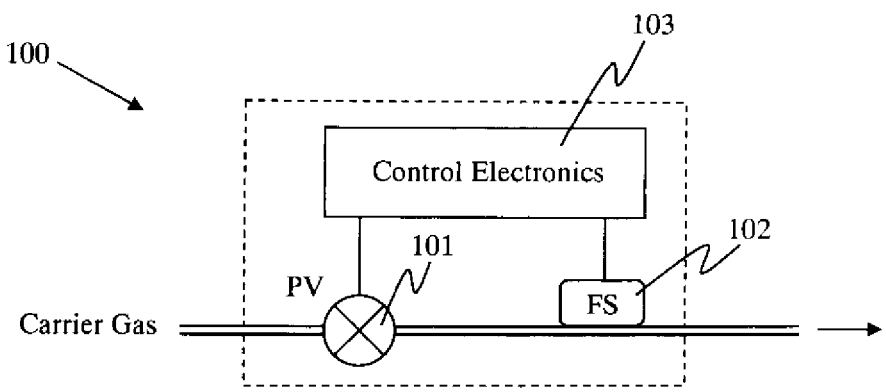
FIG. 1 shows a schematic view of a conventional mass flow controller (MFC).
Figure 2:
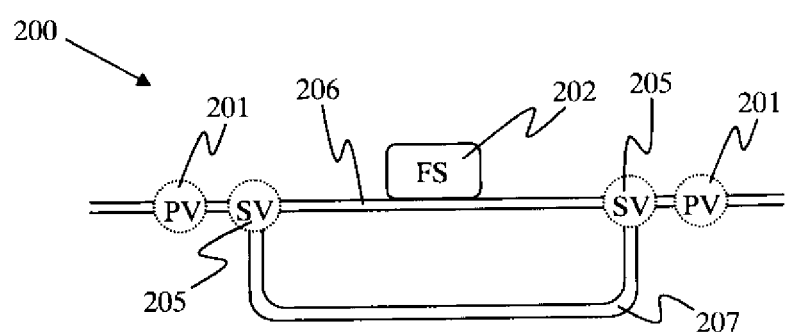
FIG. 2 shows a schematic illustrating a principle of embodiments of the invention.

As illustrated in FIG. 2, which illustrates a bypass circuit 200, a bypass flow line 207 may be connected with the main flow line 206 from a first location upstream of the mass flow sensor 202 to a second location downstream of the mass flow sensor. The switching valve 205 may be located at either the first junction (at the first location) or at the second junction (at the second location), where the main flow line 206 and the bypass flow line 207 meet. The switching valve 205 is used to direct the gas to flow through the main line 206 (and hence through the mass flow sensor 202), or to flow through the bypass flow line 207 (and hence bypassing the mass flow sensor 202). When the gas flow is directed to the bypass flow line 207, the mass flow sensor 202 would experience a zero gas flow, allowing the mass flow sensor to perform auto-zeroing.

As noted above, in MFCs, a proportional valve may be upstream of the mass flow sensor or downstream of the mass flow sensor. In accordance with embodiments of the invention, the MFCs may have proportional valves 201 upstream of the first junction or downstream of the second junction, as illustrated in FIG. 2. Thus, embodiments of the invention may include MFCs that have a switching valve upstream or downstream of a mass flow sensor, and a proportional valve upstream or downstream of the junctions, where the main flow line and the bypass flow line meet.

As used herein, the terms "upstream" and "downstream" are used in their normal meanings with respect to a fluid flow. For example, in a gas chromatograph, upstream is closer to the gas source, and downstream is farther from the gas source.

The following examples will describe some of these embodiments. For clarity of illustration, the following examples will assume the proportional valve is upstream. However, one skilled in the art would appreciate that the description also applies to alternative embodiments with the proportional valves at the downstream locations.

Figure 3:
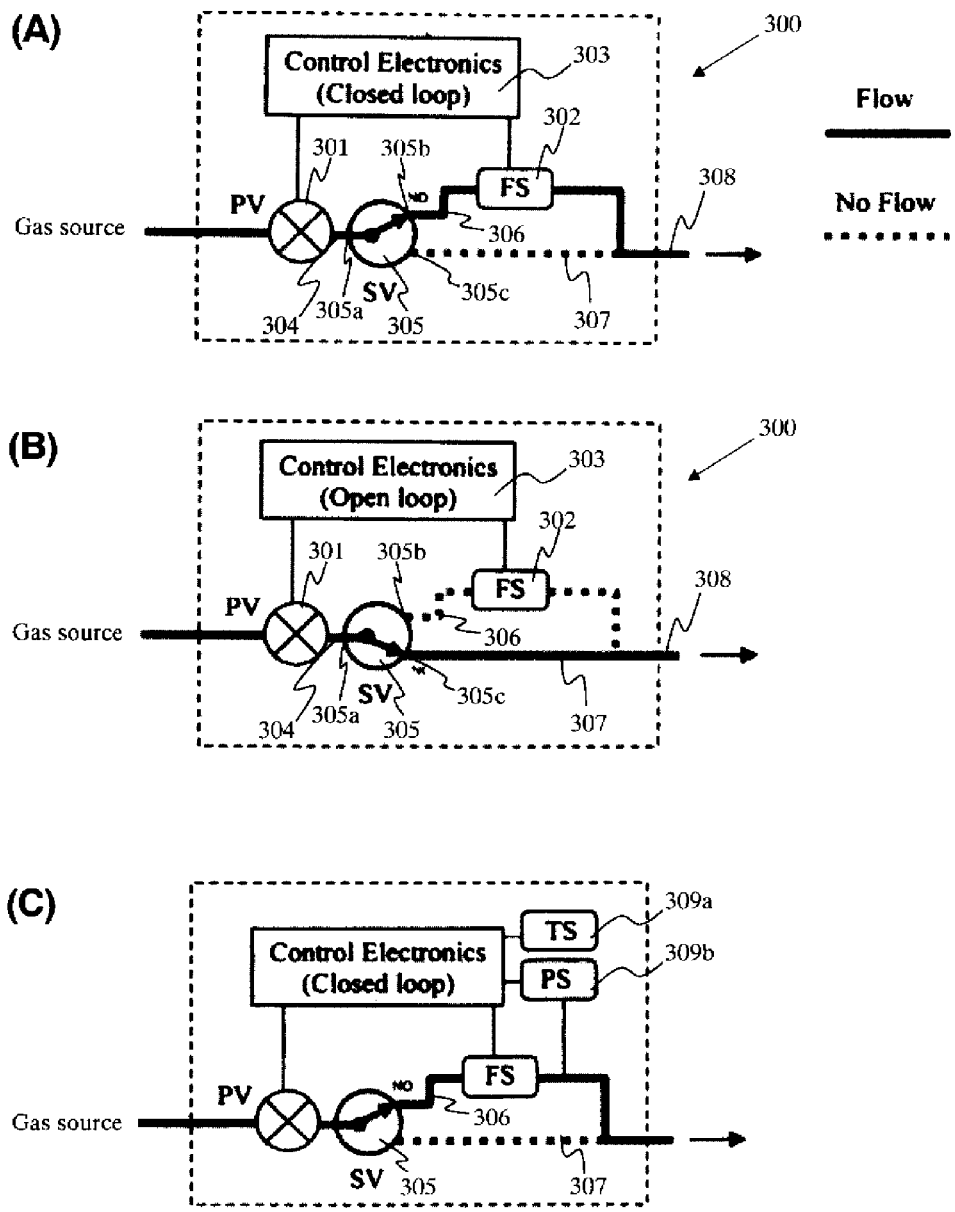
FIG. 3A shows an MFC in the normal flow state, in which the switching valve (SV) is off, in accordance with one embodiment of the invention.
FIG. 3B shows an MFC in the auto-zero state, in which the switching valve (SV) is on, in accordance with one embodiment of the invention.
FIG. 3C shows an embodiment of the invention that includes a pressure sensor (PS) and/or a temperature sensor (TS).

FIG. 3A and FIG. 3B show schematics of one embodiment of the invention, in which a switching valve is located upstream of the mass flow sensor. FIG. 3A and FIG. 3B show such an MFC in the closed-loop state and open-loop state, respectively. Referring to FIG. 3A, a mass flow controller 300 in this example comprises a proportional valve (PV) 301 and a mass flow sensor (FS) 302 connected to a control electronics (i.e., a control device) 303. A control device typically has calculating and results storage capability. It may be in a single assembly or the functions may be distributed. A control device for MFC often includes some user interface to input and/or output control values. In accordance with embodiments of the invention, a control device may include a program for holding the flow at the MFC outlet substantially constant, while the MFC is in auto-zero process. For example, such a program may send a signal from the control device to the proportional valve to actively control the function of the proportional valve, while the system is performing auto-zeroing.

In addition, a switching valve (SV) 305 is disposed between the proportional valve 301 and the mass flow sensor 302 (i.e., upstream of the mass flow sensor). The switching valve 305 comprises an inlet port 305a that is connected via flow line segment 304 to the proportional valve 301. In addition, the switching valve 305 has two outlet ports 305b and 305c. The outlet port 305b on the switching valve 305 is connected via flow line segment 306 to the mass flow sensor 302, while the outlet port 305c is connected to bypass flow line 307, which bypasses the mass flow sensor 302 and connects directly with the exit line 308 of the MFC.

As illustrated in FIG. 3A, the switching valve 305 is in the closed-loop state, in which the inlet port 305a in the switching valve 305 is connected to the outlet port 305b such that the gas flow is permitted to flow from the proportional valve 301, via the switching valve 305, to the mass flow sensor 302.

This closed-loop state corresponds to the situation when measurements are taken and active control of the proportional valve is performed. In this state, the mass flow sensor 302 performs measurements of the flow rates and sends measured signals to the control device 303. The control device 303 uses these signals and the stored calibration curve to control the proportional valve 301. In this closed-loop state of the switching valve 305, the MFC 300 is in the operation mode, in which the mass flow sensor 302 and the control electronics 303 form a feedback loop to control the proportional valve 301 so as to control a desired mass flow rate.

As noted above, calibrations of MFCs are necessary to counter various factors (such as drifting of the mass flow sensor signals) that might impact the accuracy of the signals measured by the mass flow sensors. In particular, zero-offset values from the mass flow sensor 302 should be calibrated from time to time to avoid erroneous readings. When such calibration is needed, one can switch the switching valve 305 to an open-loop state, as illustrated in FIG. 3B.

As shown in FIG. 3B, the switching valve 305 is in the open-loop state, in which the switching valve 305 has the inlet port 305a connected to the other outlet port 305c, which leads to the bypass flow line segment 307 and then to the exit line 308. In this open-loop state, the gas flow bypasses the mass flow sensor 302. Because the gas flow bypasses the mass flow sensor 302, the mass flow sensor 302 is in the zero-flow state. This permits the mass flow sensor 302 to take a measurement of the zero-offset, which can then be used to calibrate the zero flow.

As illustrated in FIG. 3B, with this embodiment, there is no need to shut off the proportional valve 301 during zero-offset calibration. Therefore, no additional positive shutoff valve is required. In addition, the gas flow is not interrupted, and the system pressure would not change, except for the brief moment during the switching of the switching valve. This makes it easier for the system to be ready for zero-offset measurements or for getting back to normal measurements.

In accordance with some embodiments of the invention, an MFC may further comprise a temperature sensor (TS) 309a and/or a pressure sensor (PS) 309b, as illustrated in FIG. 3C. The temperature sensor 309a and the pressure sensor 309b can be any suitable sensors known in the art. The pressure sensor 309b, for example, may be placed on the flow line 306 at a suitable location, such as downstream of the switching valve 305. The temperature sensor 309a may be placed anywhere on the flow line 306. Alternatively, the temperature sensor 309a may be integrated in the pressure sensor 309b or in the mass flow sensor 302. With these temperature sensors 309a and/or pressure sensors 309b, variations in the temperatures and pressures can be taken into account during the auto-zero processes and during the operation mode.

One skilled in the art would appreciate that different types of mass flow sensors are available and can be used with embodiments of the invention, such as thermal type mass flow sensors or differential pressure type flow sensors. With differential pressure type mass flow sensors, which use a differential pressure sensor to measure ΔP across a well defined flow resistor to derive a volumetric flow rate based on the ΔP and the characteristics of the flow resistor, the pressure sensors 309b shown in FIG. 3C may not be needed. Instead, the differential pressure sensor may be used for this purpose.

As noted above with reference to FIG. 2, the switching valve 205 may be placed upstream or downstream of the mass flow sensor 202. While the embodiments shown in FIGS. 3A-3C have the switching valves 305 upstream of the mass flow sensor 302, alternative embodiments with the switching valves downstream of the mass flow sensors are shown in FIGS. 4A-4C.

Figure 4:
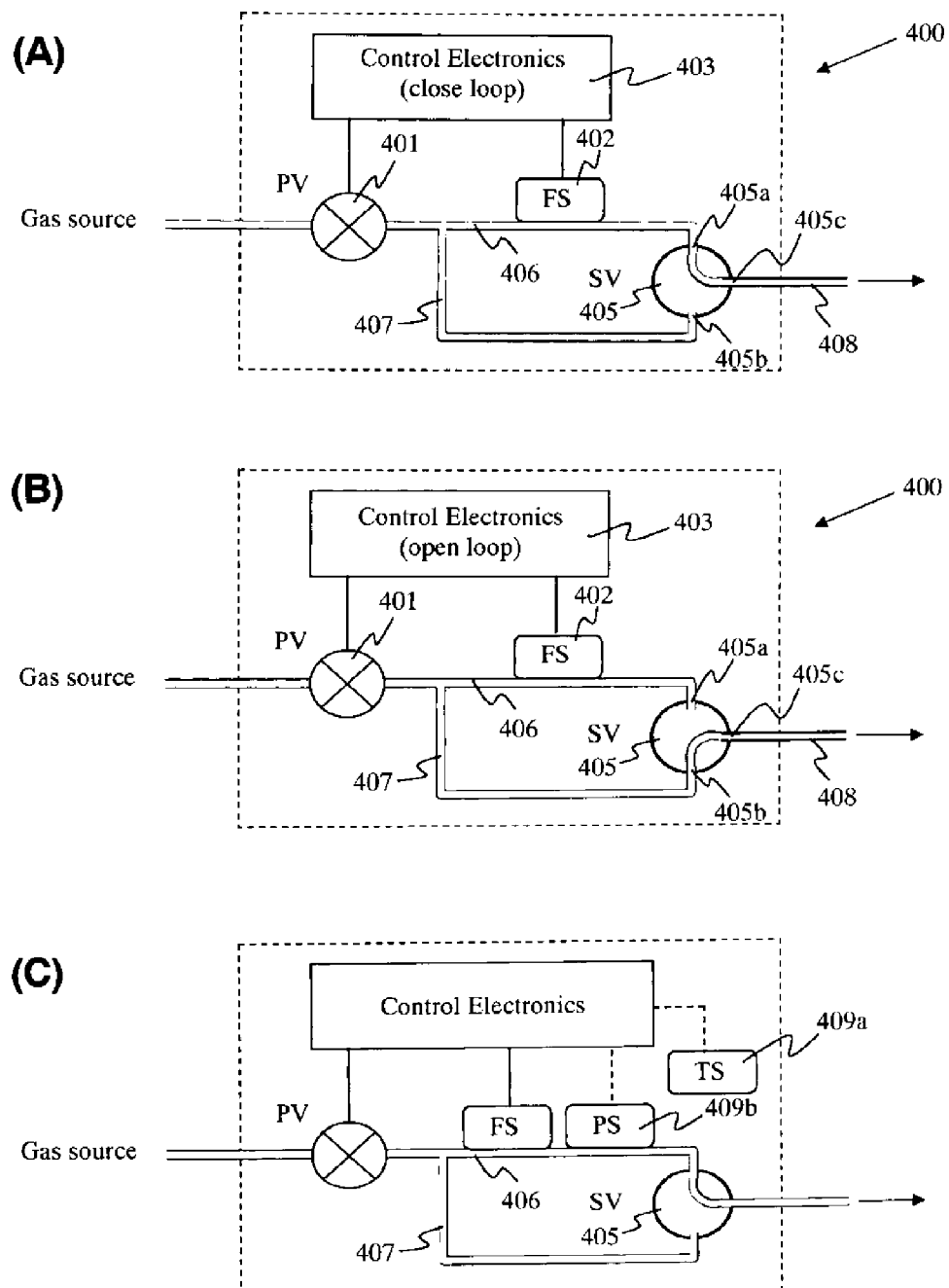
FIG. 4A shows an MFC in the normal flow state, in which the switching valve (SV) is off, in accordance with one embodiment of the invention.
FIG. 4B shows an MFC in the auto-zero state, in which the switching valve (SV) is on, in accordance with one embodiment of the invention.
FIG. 4C shows an embodiment of the invention that includes a pressure sensor (PS) and/or a temperature sensor (TS).

As shown in FIG. 4A, the MFC 400 comprises a proportional valve 401 and a mass flow sensor 402 connected to a control electronics (i.e., a control device) 403. A gas source is connected to the proportional valve 401, which is then connected to the mass flow sensor 402 via a first flow line 406. Downstream of the mass flow sensor 402, the first flow line 406 is connected to a switching valve 405 at its first input port 405a.

A second flow line 407 is connected at its first end to the first flow line 406 at a location (first junction) between the proportional valve 401 and the mass flow sensor 402. The second end of the second flow line 407 is connected to the switching valve 405 via its second input port 405b. The switching valve 405 further includes an output port 405c, which is connected to an exit line 408.

As shown in FIG. 4A, the switching valve 405 connects the first flow line 406 to the exit line 408. In this state (the closed-loop state), the gas can flow from the source through the proportional valve 401, via the first flow line 406, to the mass flow sensor 402 and the switching valve 405 and finally to the exit line 408. In this operation mode, the MFC 400 can regulate the flow of the gas by controlling the proportional valve 401 based on signals received from the mass flow sensor 402.

As shown in FIG. 4B, when auto-zero is needed, the switching valve 405 is switched to an open-loop state, in which the gas can flow from the source through the proportional valve 401 to the second flow line 407 and then to the switching valve 405. This path bypasses the mass flow sensor 402. Therefore, the mass flow sensor 402 is in the zero-flow state. A measurement made by the mass flow sensor 402 at the zero-flow state would provide a zero-offset, which can be used to calibrate the readings in the operation mode.

In accordance with some embodiments of the invention, an MFC 400 illustrated in FIG. 4A or FIG. 4B may further comprise a temperature sensor 409a and/or a pressure sensor 409b, as shown in FIG. 4C. The pressure sensor 409b a, for example, may be placed on the first flow line 406 or second flow line 407 at any suitable locations, including downstream of the switching valve 405. Similarly, the temperature sensor 409a may be placed anywhere on the first flow line 406 or the second flow line 407. Alternatively, the temperature sensor 409a may be integrated in the pressure sensor 409b or in the mass flow sensor 402. With these temperature sensors 409a and pressure sensors 409b, variations in the temperatures and pressures can be taken into account during the auto-zero processes and during the operation mode. Furthermore, the pressure sensor readings may be used to control the flow when the flow is temporarily switched away from the mass flow sensor 402 during an auto-zero process. This will be described in detail later.

The above description illustrates some exemplary embodiments of the invention. These examples are for illustration only and are not meant to limit the scope of the invention. One of ordinary skill in the art would appreciate that other variations and modifications of these examples are possible without departing from the scope of the invention. For example, while the above examples all have the proportional valves upstream of the mass flow sensors, the invention also encompasses embodiments that have the proportional valves downstream of the mass flow sensors.

With embodiments of the invention, auto-zeroing may take place any time, such as at a fixed frequency (e.g., once every 60 seconds) or following any suitable schedule. How often one performs the auto-zeroing may depend on the rates of variations caused by factors that may lead to zero-offset shifts. Alternatively, the auto-zeroing can also be triggered on-demand. For example, a temperature sensor may optionally be included either inside or near the MFC to monitor the ambient temperature changes. If it is detected that the temperature variation exceeds a pre-defined threshold, an auto-zero process may be activated.

One advantage of an embodiment of the invention is that the gas flow at the outlet of an MFC is not disrupted during the auto-zero processes. Thus, during an auto-zero process, the proportional valve may continue to function or be regulated by the control device to maintain the normal operation of the proportional valve. Various approaches may be used to allow the proportional valve to be actively controlled during an auto-zero process. For example, "pseudo" signals may be sent from the control device to the proportional valve during the auto-zero process, as if the system were still in the normal operation mode.

The pseudo signals that may be used to control the proportional valve during an auto-zero process may come from many sources, including mass flow sensors, proportional valves, and pressure sensors. For example, the pseudo signals may be predicted (projected) values based on the historical readings of the mass flow sensor prior to the start of the auto-zeroing, or the pseudo signals may be the last readings of the mass flow sensor prior to the start of the auto-zeroing. The prediction (or projection) may use any suitable form, such as linear projection. In addition to using signals from the mass flow sensor, the pseudo signals may be based on readings from other devices, such as proportional valve drive signals, temperature sensor signals, or pressure sensor signals.

For example, the pseudo signals may be obtained by reading the value of the closed-loop (normal operation mode) proportional valve drive just before the three-way switching valve is turned on to bypass the mass flow sensor. Such last reading may be used to create a "fixed duty cycle" for the proportional valve device—i.e., to fix or maintain the proportional valve operation during the auto-zero process. That is, the proportional valve drive may be locked at this value for the duration of the time the flow is diverted around the mass flow sensor by the action of the three-way switching valve. Alternatively, one may project (extrapolate) what the proportional valve readings should be during the auto-zero processes and use such projected (extrapolated) values to control the proportional valve during the auto-zero processes. The projection or extrapolation may be based on a simple linear function or any suitable functions.

In other examples, the pseudo signals may be based on pressure sensor or temperature sensor signals. In this approach, the control device may control the proportional valve drive based on the pressure or temperature sensor signals. For example, one may use pressure signals from the pressure sensor before switching to the auto-zero mode or with a suitable projection into the short switched duration if necessary.

In sum, the various control signals (pseudo signals) that may be used to control the proportional valves during auto-zeroing may come from any suitable sensors or devices (e.g., mass flow sensors, proportional valves, pressure sensors, or temperature sensors). The signals may be the readings of the devices or sensors immediately prior to switching to the auto-zero mode and the control signals (pseudo signals) are locked at these values. Alternatively, the pseudo signals may be projected (extrapolated) signals. Similarly, the pseudo signals may be a combination of the fixed readings (e.g., the readings immediately prior to the switching) and any suitable modulation signals.

Figure 5A:
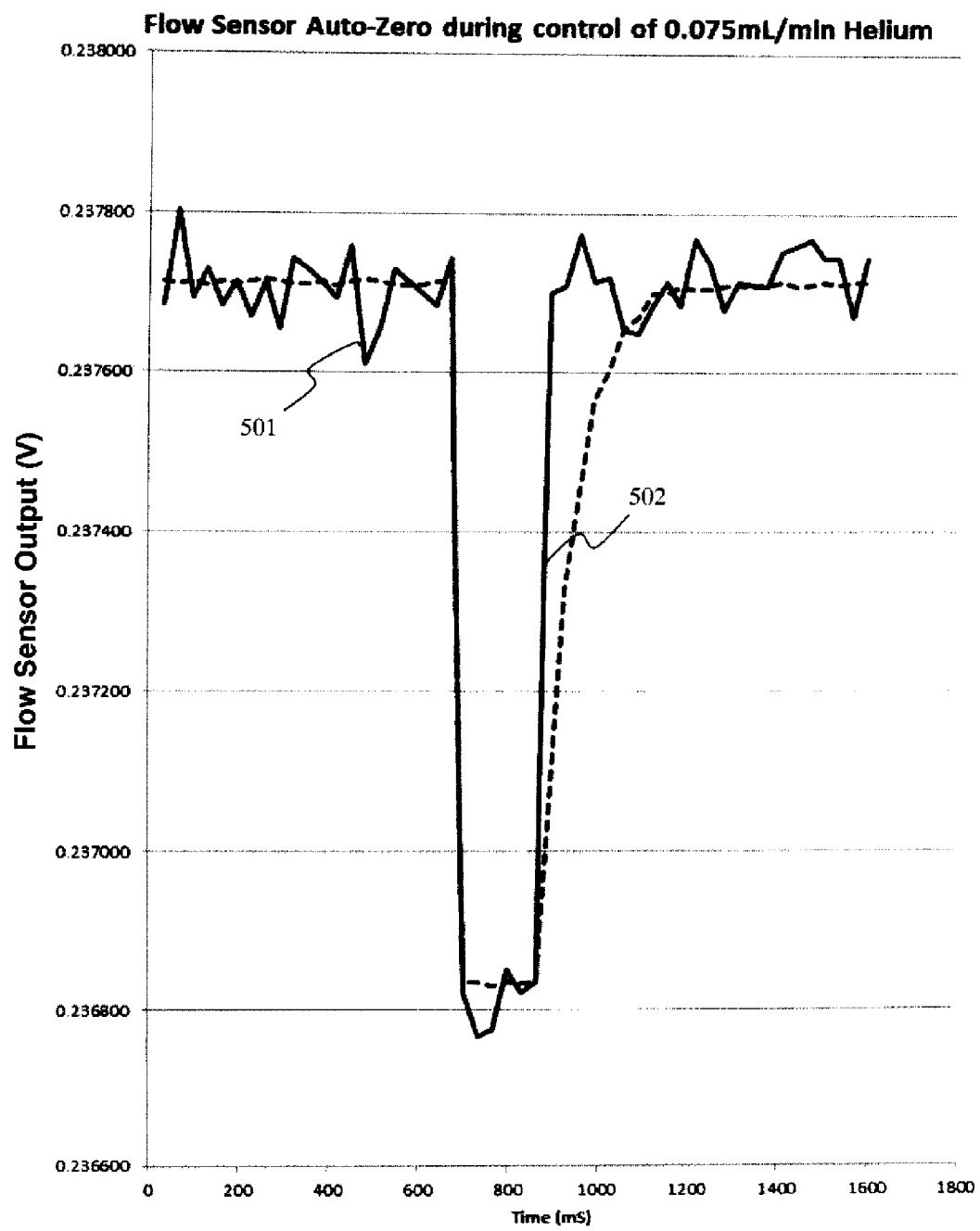
FIG. 5(A) and FIG. 5(B) show results of an auto-zeroing of an MFC in accordance with one embodiment of the invention.
Figure 5B:
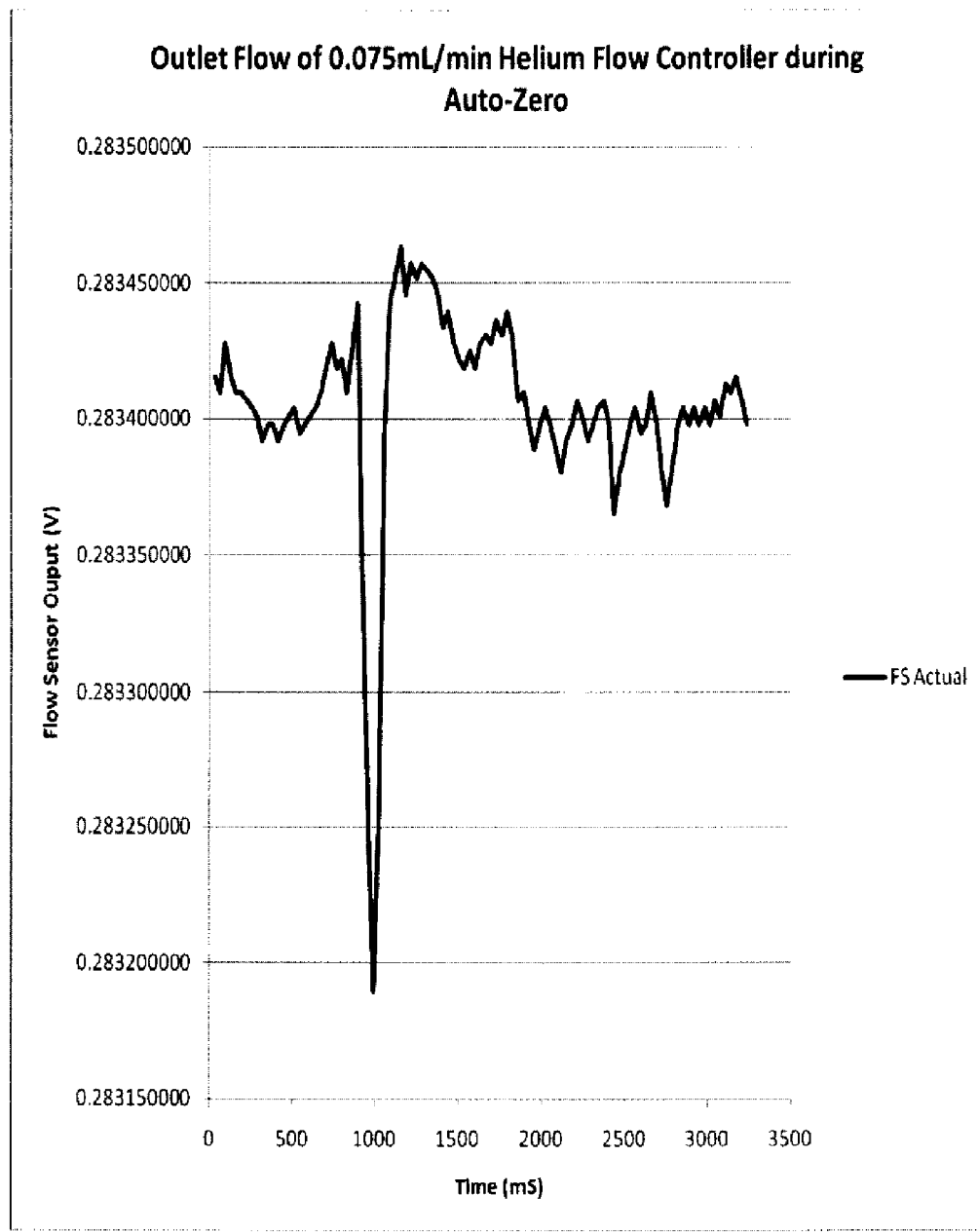

FIG. 5A and FIG. 5B show results from a test run of an auto-zero process using an MFC in accordance with one embodiment of the invention, as shown in FIGS. 3A-3C. The control program is modified using the Agilent VEE (Visual Engineering Environment) program. In this test, the gas flow is diverted from the mass flow sensor for a brief duration. In FIG. 5A, which shows readings from the mass flow sensor during a switch over to an auto-zero process, the noisy line 501 is the raw mass flow sensor reading, and the smooth line 502 is a filtered version of the mass flow sensor signal. In FIG. 5B, the mass flow sensor readings for a period longer than 10 times the switch over duration (i.e., auto-zero duration) are shown. The results in FIG. 5B show that the flow is maintained substantially constant during the period.

In general, using embodiments of the invention, the auto-zero process can be performed with a short duration (such as a few seconds) to divert the gas flow away from the mass flow sensor. The duration may be, for example 3 seconds or less, preferably 2 seconds or less, more preferably less than 1 second. For example, the test in FIG. 5 shows that a rather short period of less than 1 second is sufficient for the auto-zero process.

One important characteristic for auto-zero is the repeatability of the results. Embodiments of the invention have been tested under various conditions and the variations in the zero-offset readings typically are within a few percent.

Figure 6B:
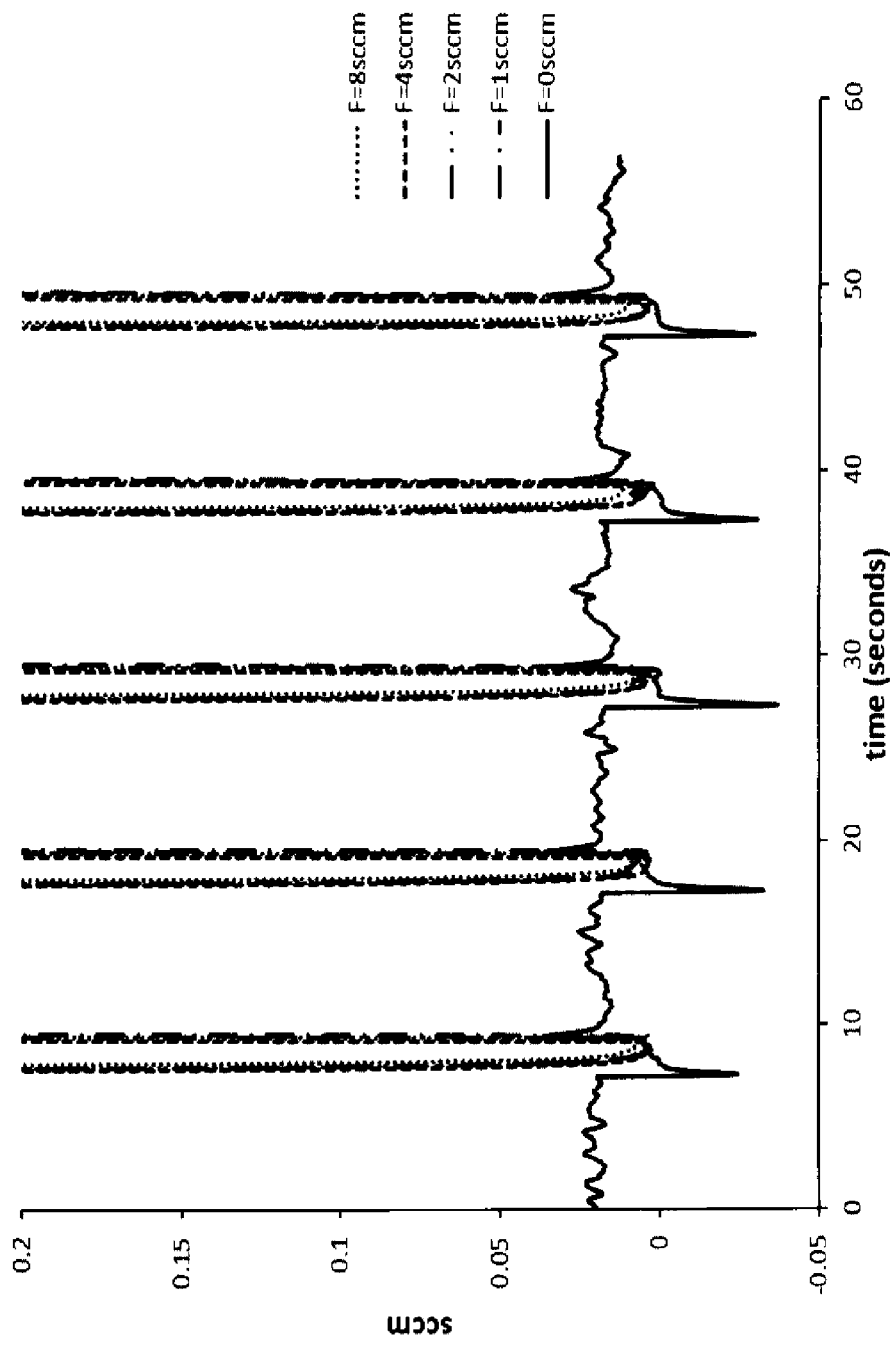
FIG. 6B shows an expanded region of the chart in FIG. 6A to show the near zero regions.

In another experiment, an MFC as shown in FIGS. 4A-4C is used. FIG. 6A shows mass flow sensor data for different gas flow rates, ranging from 8 sccm down to 0 sccm, using a 2-second auto-zero duration. In these tests, the flows are passed through the mass flow sensors for 8 seconds and then diverted to the bypass flow line for 2 seconds. It is clear from the results that regardless of the flow rates, the 2 second duration for auto-zeroing is sufficient to create a stable zero flow condition for auto-zeroing. FIG. 6B shows the expanded region near the zero flow rates. This graph shows the true zero flow rates detected by the mass flow sensor using an MFC of the invention. FIG. 6B also shows the leak rate (about 0.024 sccm) of the proportional valve.

From the above experiments, it is clear that embodiments of the invention have several advantages. An MFC of the invention can provide true zero flow rates for reliable auto-zero processes. The auto-zero process can be very brief (milliseconds to second range) and there is no need to interrupt the gas flow in the system. Furthermore, embodiments of the invention can be used to maintain constant flows during auto-zero processes.

Figure 7:
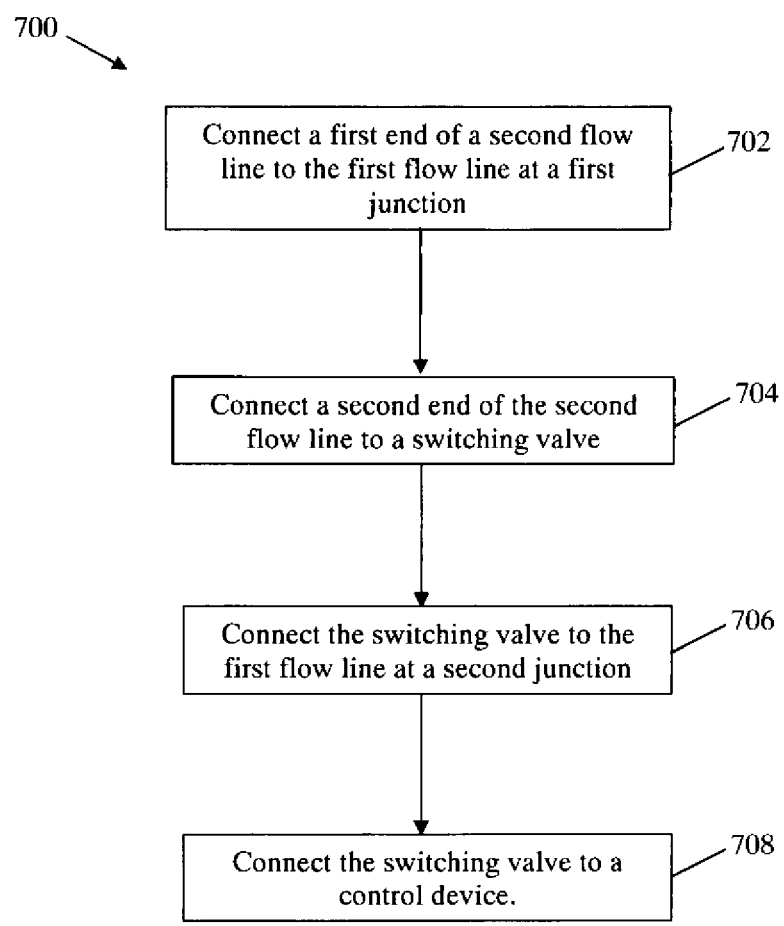
FIG. 7 shows a method for manufacturing an MFC in accordance with one embodiment of the invention.

Some embodiments of the invention relate to methods for manufacturing MFCs described above. FIG. 7 shows an exemplary method of the invention for manufacturing an MFC that comprises a proportional valve connected to a mass flow sensor via a first flow line. The MFC also comprises a control device that is connected with the proportional valve and the mass flow sensor to form a feedback control loop for regulating the proportional valve based on signals measured by the mass flow sensor. The methods may include modification of conventional MFCs or manufacturing an MFC from various components.

As shown in FIG. 7, a method 700 in accordance with one embodiment of the invention includes: connecting a first end of a second flow line to the first flow line at a first junction (step 702); connecting a second end of the second flow line to a switching valve (step 704); and connecting the switching valve to the first flow line at a second junction (step 706). One of the first junction and the second junction is located upstream of the mass flow sensor and the other is located downstream of the mass flow sensor, as illustrated in FIG. 2.

As used herein, the "connecting" or "joining" of the first flow line and the second flow line may be by any means known in the art, such as using a T-adaptor or a Y-adaptor. When a switching valve (such as a 3-way switching valve) is placed at one of these junctions, the two flow lines are connected to the appropriate ports on the switching valve. Such techniques are well known in the art.

The method may further comprise connecting the switching valve to a control device (step 708). The switching valve may be connected to the control device that also controls the flow sensor and/or the proportional valve. Alternatively, the switching valve may be connected to a separate control device for controlling the functions of the switching valve. A switching valve for use with embodiments of the invention is capable of switching between two flow lines, as illustrated in FIG. 2. A suitable switching valve may be a 3-way switching valve; however, one skilled in the art would appreciate that two two-way valves may be used instead to accomplish the same purpose. Similarly, latching solenoid valves may also be used. In this description, 3-way valves are used for clarity of illustration. However, such examples are not meant to limit the scope of the invention. In this description, the term "switching valve" may be used as a generic term that encompasses a 3-way switching valve or other valve configurations that would accomplish the same purpose.

The method illustrated in FIG. 7 may be applied to modify a conventional MFC. Some methods of the invention relate to manufacturing an MFC from various components. For example, one such method may includes the following steps:

Providing a proportional valve and connecting its inlet to a gas source.

Providing a first flow line with one of its ends connected to the proportional valve outlet, and the other end to the common port of a 3-way switching valve.

Providing a second flow line with one of its ends connected to the first output port (which may be one of the NO port (normally open port) or the NC port (normally closed port)) of the 3-way switching valve and the other end to the input port of a mass flow sensor that measures flow in the second flow line at a position downstream of the proportional valve outlet.

Providing a third flow line with one of its ends connected to the second outlet port (which would be the other of the NC port or the NO port) of the 3-way switching valve and the other end to an exit line of the MFC that is connected to the outlet of the mass flow sensor.

Providing an open loop control of the proportional valve so as to control a desired mass flow at the common port of the switch valve when the switch valve is on for a short period time. In addition, the control device can provide an open loop control of the proportional valve so as to control a desired mass flow at the common port of the switching valve when the switch valve is on for a short period time. The typical time duration for the switching valve to be on (i.e., auto-zero processing) may be less than 3 seconds, preferably less than 1 second, during which the mass flow sensor measures a new zero-offset.

Furthermore, one may optionally provide a scheduling or triggering mechanism to control the 3-way switching valve.

Similarly, another example of a method may include the following steps:

Providing a proportional valve and connecting its inlet to a gas source.

Providing a first flow line with one of its ends connected to the proportional valve outlet.

Providing a mass flow sensor that measures flow in the first flow line at a position downstream of the proportional valve outlet.

Providing a second flow line with one of its ends connected to the first flow line at a position downstream of the proportional valve outlet and upstream of the mass flow sensor.

Providing a switching valve (e.g., a 3-way switching valve) that has its normally closed port (NC port) or normally open port (NO port) connected to the other end of the second flow line, and the other port of the switching valve (i.e., the NO port or the NC port) connected to the other end of the first flow line downstream of the mass flow sensor.

Providing a control electronics (i.e., a control device) to provide feedback control between the proportional valve and the mass flow sensor as the switch valve is off.

Providing an open loop control of the proportional valve so as to control a desired mass flow at the common port of the switch valve when the switch valve is on for a short period time. In addition, the control device can provide an open loop control of the proportional valve so as to control a desired mass flow at the common port of the switching valve when the switch valve is on for a short period time. The typical time duration for the switching valve to be on (i.e., auto-zero processing) may be less than 3 seconds, during which the mass flow sensor measures a new zero-offset.

Furthermore, one may optionally provide a scheduling or triggering mechanism to control the 3-way switching valve.

Figure 8:
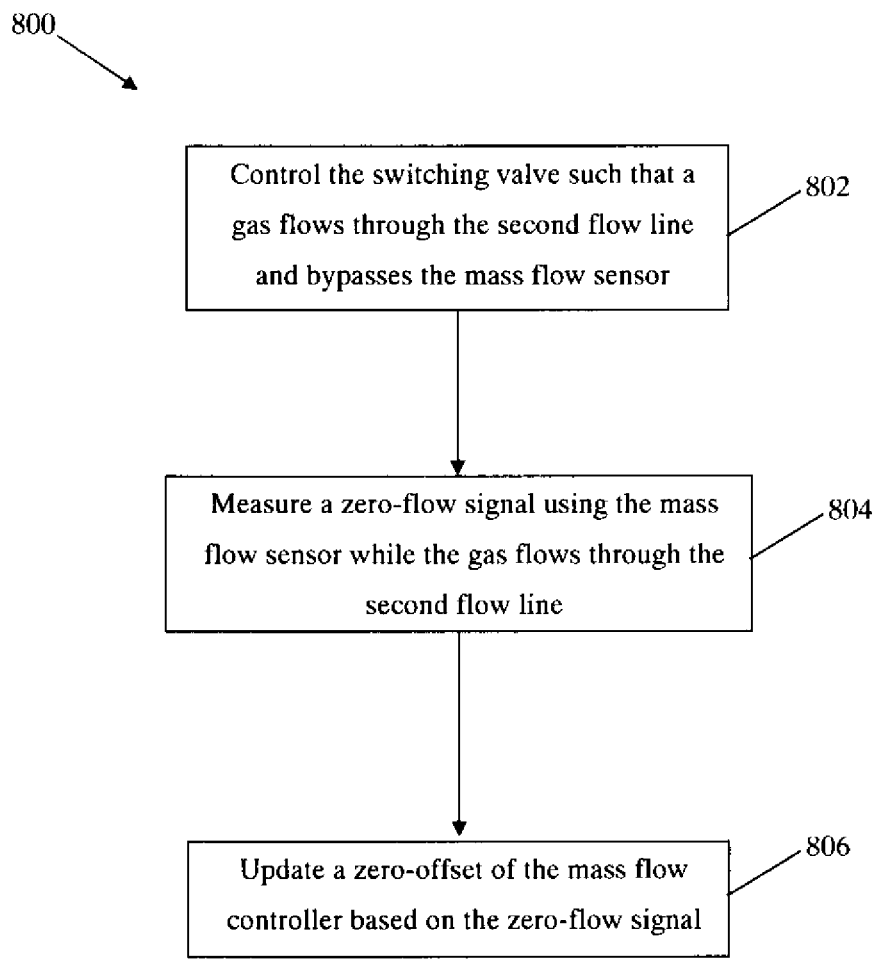
FIG. 8 shows a method for auto-zeroing an MFC in accordance with one embodiment of the invention.

Some embodiments of the invention relate to methods for auto-zeroing an MFC in accordance with embodiments of the invention. As shown in FIG. 8, a method 800 for performing auto-zeroing of an MFC may includes the following steps: controlling the switching valve such that a gas flows through the second flow line and bypasses the mass flow sensor (step 802); measuring a zero-flow signal using the mass flow sensor while the gas flows through the second flow line (step 804); and updating a zero-offset of the mass flow controller based on the zero-flow signal (step 806).

Embodiments of the invention may include one or more of the following advantages. The invention provides mass flow controllers that can be calibrated without shutting off the gas flows. In addition, the invention provides methods for calibrating zero-offset; such calibration can be used to compensate for drifts of the mass flow sensor signals caused by many different reasons with a universal approach. These methods can be readily implemented in existing equipment with minimal modifications.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. A mass flow controller, comprising:
a proportional valve having a first port connected to a first external line;
a mass flow sensor;
a first flow line connecting from a second port of the proportional valve through the mass flow sensor to a second external line, wherein one of the first external line and the second external line is an entry line for connection to a fluid source and the other of the first external line and the second external line is an exit line;
a second flow line joining the first flow line at a first junction located upstream of the mass flow sensor and at a second junction located downstream of the mass flow sensor;
a switching valve placed at the first junction or the second junction to join the first flow line and the second flow line such that the switching valve can regulate a flow of a fluid through the first flow line or the second flow line, wherein the switching valve is switchable between a first state at which the switching valve allows the fluid to flow through the first flow line, and a second state at which the switching valve allows the fluid to flow through the second flow line while producing a zero-flow condition at the mass flow sensor; and a feedback control comprising control electronics and a feedback control loop connecting the control electronics with the proportional valve and the mass flow sensor, said feedback control configured to regulate the proportional valve based on signals measured by the mass flow sensor, wherein the feedback control is configured to send a control signal to the proportional valve effective for keeping a flow rate of fluid exiting the exit line substantially constant while the switching valve is in the second state and the fluid is flowing through the second flow line.

2. The mass flow controller of claim 1, wherein the switching valve is placed at the first junction.

3. The mass flow controller of claim 1, wherein the switching valve is placed at the second junction.

4. The mass flow controller of claim 1, further comprising a sensor selected from the group consisting of: a pressure sensor; a temperature sensor; and both of the foregoing.

5. The mass flow controller of claim 4, wherein the temperature sensor is integrated with the flow sensor or the pressure sensor.

6. The mass flow controller of claim 1, wherein the proportional valve is upstream of the mass flow sensor.

7. The mass flow controller of claim 1, wherein the feedback control is configured to perform auto-zeroing, while the switching valve is in the second state, by:
receiving a zero-flow signal from the mass flow sensor; and
updating a zero-offset value of the mass flow controller based on the zero-flow signal.

8. The mass flow controller of claim 1, wherein the feedback control is configured to send the control signal to the proportional valve based on a measurement made by the mass flow sensor prior to the switching valve being switched to the second state.

9. The mass flow controller of claim 1, wherein the feedback control is configured to send the control signal to the proportional valve based on a measurement made by a sensor after the switching valve is switched to the second state, and the sensor is selected from the group consisting of: a pressure sensor; a temperature sensor; and both of the foregoing.

10. The mass flow controller of claim 1, wherein the feedback control is configured to control switching of the switching valve between the first state and the second state.

* * * * *